US011241374B2

(12) United States Patent
Chen et al.

(10) Patent No.: US 11,241,374 B2
(45) Date of Patent: Feb. 8, 2022

(54) COMPOSITIONS AND METHODS FOR TREATING SKIN CONDITIONS USING LIGHT AND GLUCOSAMINE HYDROCHLORIDE

(71) Applicant: Johnson & Johnson Consumer Inc., Skillman, NJ (US)

(72) Inventors: Michelle Chen, Skillman, NJ (US); Ali Fassih, Flemington, NJ (US); Jennifer M. Li, Piscataway, NJ (US); Wen-Hwa Li, Cranbury, NJ (US); Liliam A. Moreira, Lake Hiawatha, NJ (US); Ramine Parsa, Lawrenceville, NJ (US); Michael D. Southall, Pennington, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 569 days.

(21) Appl. No.: 16/021,748

(22) Filed: Jun. 28, 2018

(65) Prior Publication Data

US 2020/0000696 A1  Jan. 2, 2020

(51) Int. Cl.
| | | |
|---|---|---|
| *A61K 8/00* | (2006.01) | |
| *A61K 8/60* | (2006.01) | |
| *A61K 8/02* | (2006.01) | |
| *A61K 8/23* | (2006.01) | |
| *A61K 8/362* | (2006.01) | |
| *A61K 8/365* | (2006.01) | |
| *A61M 37/00* | (2006.01) | |
| *A61N 5/06* | (2006.01) | |
| *A61Q 19/00* | (2006.01) | |
| *A61Q 19/08* | (2006.01) | |

(52) U.S. Cl.
CPC ............ *A61K 8/602* (2013.01); *A61K 8/0233* (2013.01); *A61K 8/23* (2013.01); *A61K 8/362* (2013.01); *A61K 8/365* (2013.01); *A61M 37/0092* (2013.01); *A61N 5/062* (2013.01); *A61Q 19/007* (2013.01); *A61Q 19/08* (2013.01); *A61M 2037/0007* (2013.01); *A61N 2005/0659* (2013.01); *A61N 2005/0663* (2013.01)

(58) Field of Classification Search
CPC .... A61K 8/0208; A61K 8/0233; A61K 8/602; A61K 8/0216; A61K 8/23; A61K 8/362; A61K 8/60; A61K 8/19; A61K 8/365; A61Q 19/007; A61Q 19/08; A61M 37/0092; A61N 5/062
See application file for complete search history.

(56) References Cited

U.S. PATENT DOCUMENTS

| | | | |
|---|---|---|---|
| 7,066,941 B2 | 6/2006 | Perricone | |
| 7,480,530 B2 * | 1/2009 | Sun | A61N 1/044 604/20 |
| 7,776,915 B2 | 8/2010 | Morariu | |
| 8,231,292 B2 | 7/2012 | Rabe et al. | |
| 8,771,328 B2 | 7/2014 | Tapper et al. | |
| 9,676,696 B2 | 6/2017 | Hakozaki | |
| 2004/0049247 A1 | 3/2004 | Perricone | |
| 2004/0260210 A1* | 12/2004 | Ella | A61H 9/005 601/7 |
| 2006/0217690 A1 | 9/2006 | Bastin et al. | |
| 2006/0235370 A1 | 10/2006 | Oblong et al. | |
| 2006/0263309 A1 | 11/2006 | Bissett | |
| 2007/0092469 A1 | 4/2007 | Jacobs | |
| 2008/0031833 A1 | 2/2008 | Oblong et al. | |
| 2008/0069784 A1 | 3/2008 | Millikin et al. | |
| 2008/0254055 A1 | 10/2008 | Oblong et al. | |
| 2009/0143714 A1 | 6/2009 | Millikin et al. | |
| 2010/0016782 A1 | 1/2010 | Oblong | |
| 2010/0204317 A1 | 8/2010 | Hunt et al. | |
| 2011/0224598 A1 | 9/2011 | Barolet | |
| 2014/0163651 A1 | 6/2014 | Bickford | |
| 2014/0271512 A1* | 9/2014 | Ciraldo | A61Q 19/08 424/63 |
| 2014/0277293 A1 | 9/2014 | Jagdeo et al. | |
| 2014/0303547 A1 | 10/2014 | Loupis et al. | |
| 2015/0150770 A1 | 6/2015 | Morariu | |
| 2015/0182990 A1 | 7/2015 | Binner et al. | |
| 2015/0182991 A1 | 7/2015 | Binner et al. | |
| 2015/0182992 A1 | 7/2015 | Binner et al. | |
| 2015/0182993 A1 | 7/2015 | Binner et al. | |
| 2016/0016001 A1 | 1/2016 | Loupis et al. | |
| 2016/0045758 A1 | 2/2016 | Tapper et al. | |

(Continued)

FOREIGN PATENT DOCUMENTS

| | | | |
|---|---|---|---|
| EP | 1824561 A | 8/2007 | |
| FR | 3029784 A | 6/2016 | |

(Continued)

OTHER PUBLICATIONS

Leite et al., Skin Delivery of Glucosamine and Chondroitin Sulphates—A Perspective on the Conservative Treatment for Osteoarthritis of the Knee, Journal of Biosciences and Medicines, 2017, 5, 11-20. (Year: 2017).*

Anitua et al., Platelet-released growth factors enhance the secretion of hyaluronic acid and induce hepatocyte growth factor production by synovial fibroblasts from arthritic patients, Rheumatology 2007;46:1769-1772. (Year: 2007).*

(Continued)

*Primary Examiner* — Susan T Tran

(74) *Attorney, Agent, or Firm* — Sharon E. Hayner

(57) ABSTRACT

The present invention provides compositions, methods and kits for treating skin, which combine administration of glucosamine hydrochloride and red light having a peak wavelength of about 600 nm to about 750 nm, near infrared light having a peak wavelength of about 750 nm to about 1000 nm, or both.

10 Claims, No Drawings

(56) References Cited

U.S. PATENT DOCUMENTS

2016/0107004 A1* 4/2016 Wilder ............... A45D 33/38
                                                    604/290
2016/0367490 A1   12/2016 Binner et al.

FOREIGN PATENT DOCUMENTS

| WO | WO 2009/010921 A | 1/2009 |
| WO | WO 2014/138930 A | 9/2014 |
| WO | WO 2015/149177 A | 10/2015 |
| WO | WO 2016/096594 A | 6/2016 |
| WO | WO 2016/146778 A | 9/2016 |

OTHER PUBLICATIONS

Bissett Glucosamine: an ingredient with skin and other benefits, 2006 Blackwell Publishing Journal of Cosmetic Dermatology, 5, 309-315. (Year: 2006).*

European search report and written opinion dated Oct. 30, 2019, for EP application 19183252.6.

International Cosmetic Ingredient Dictionary and Handbook, eds. Pepe, Wenninger and McEwen, pp. 2930-2936 and 2962-2971; The Cosmetic, Toiletry, and Fragrance Assoc., Washington, D.C., 9th Edition, 2002.

* cited by examiner

COMPOSITIONS AND METHODS FOR TREATING SKIN CONDITIONS USING LIGHT AND GLUCOSAMINE HYDROCHLORIDE

FIELD OF THE INVENTION

Hyaluronic acid is found in all connective tissue. In skin, it is produced by fibroblasts and keratinocytes. Hyaluronic acid can bind 1000 times its weight in water, and may help the skin retain and maintain water. In young skin, hyaluronic acid is located at the periphery of collagen and elastin fibers and where these fibers intersect. Aged skin, which is less plump than young skin, is characterized by decreased levels of hyaluronic acid. Such decreased hyaluronic acid levels contribute to its disassociation with collagen and elastin as well as reduced water binding. Decreased hyaluronic acid levels are therefore implicated in signs of skin aging, including wrinkling, altered elasticity, reduced turgidity and diminished capacity to support the microvasculature of the skin. The main clinical signs of skin aging are the appearance of fine lines and wrinkles, which increase with age.

Different products and methods have been proposed for combating wrinkles and fine lines, and hyaluronic acid itself is commercially used as an active agent in both injectable and topical cosmetic products to increase moisturization and elasticity of the skin. However, hyaluronic acid has a limited lifetime on the skin and when injected into the skin. Hyaluronidases, enzymes present in skin, decompose hyaluronic acid and thus reduce its impact. The half-life of hyaluronic acid varies from one tissue to another, but it is approximately one day at the dermis and epidermis. Moreover, penetration of exogenous hyaluronic acid into the skin has proved difficult to accomplish by topical application due to its size.

Glucosamine in the form or oral supplements is marketed to support the structure and function of joints in humans and animals. Commonly sold forms of glucosamine are glucosamine sulfate, glucosamine hydrochloride, and N-acetylglucosamine.

Glucosamine is used in some oral supplements for treatment of joint pain. it is not widely used in skin care.

Light therapy is also known to be effective for treating skin conditions, and it is known that red light having a wavelength of about 633 nm has an anti-inflammatory effect. The mechanism of anti-inflammation action of red light is thought to occur by inhibition of inflammatory mediators and enzymes such as interleukin-la and matrix metalloproteinases.

U.S. Pat. No. 8,771,328 discloses improved phototherapy systems comprising a therapeutic lamp platform for radiant lamps such as LED's disposed in a convenient device that may be in the form of a facial mask. The system emits different wavelengths of radiant energy, for example at least two of blue, red, or infrared.

The NEUTROGENA Light Therapy Acne Mask, commercially available from Johnson & Johnson Consumer Inc., emits blue light to penetrate just beneath the skin's surface to kill acne-causing bacteria, and red light that penetrates deeper into the skin to reduce inflammation.

U.S. Pat. No. 7,066,941 relates to the treatment of aging or damaged skin by irradiating it with an effective amount of visible light having a wavelength of about 400 nm to about 500 nm. The light source may be sunlight or artificial light for example, and in one embodiment, light-emitting diodes are applied to discrete skin areas. Compositions containing compounds that enhance light penetration of the stratum corneum such as alpha-hydroxy acids and/or filter light may be applied to the skin prior to or during phototreatment.

WO 2016/146778 relates to cosmetic methods of providing skin care comprising illuminating the skin of a subject with one or more light beams that provide light to the skin having a discontinuous spectrum with peaks in wavelengths corresponding to green light, red light, and near infrared light along with a topical composition that may contain a wide variety of ingredients, including glucosamine. Such methods are said to be beneficial for skin activation processes involving proliferation and migration of skin cells and production of extracellular matrix fibers such as collagen.

Applicants have now discovered that the production of hyaluronic acid by skin may be surprisingly upregulated by application of a topical composition comprising up to about 2 weight percent of glucosamine hydrochloride and exposure of said skin to red and near infrared light using a light delivery device, thus providing significant and unexpected benefits for skin, including improving, reducing, inhibiting, or delaying the appearance of at least one sign of aging in skin. The combination may also enhance skin barrier protection and skin moisturization. Accordingly, new methods of treating signs of skin aging and moisturizing skin, for example, are now available.

SUMMARY OF THE INVENTION

The present invention provides a method of increasing the production of hyaluronic acid by skin, comprising topically applying to such skin a topical composition comprising up to about 2 weight percent of glucosamine hydrochloride and exposing said skin to red light having a peak wavelength of about 600 nm to about 750 nm, near infrared light having a peak wavelength of about 750 nm to about 1000 nm, or both, using a light delivery device.

The present invention also provides a method of treating skin, comprising topically applying to skin in need of treatment for signs of skin aging a topical composition comprising up to about 2 weight percent of glucosamine hydrochloride and exposing said skin to red light having a peak wavelength of about 600 nm to about 750 nm, near infrared light having a peak wavelength of about 750 nm to about 1000 nm, or both, using a light delivery device.

The present invention further provides a method of treating skin, comprising topically applying to skin in need of moisturization a topical composition comprising up to about 2 weight percent of glucosamine hydrochloride and exposing said skin to red light having peak wavelength of about 600 nm to about 750 nm, near infrared light having a peak wavelength of about 750 nm to about 1000 nm, or both, using a light delivery device.

The invention also provides a kit comprising: (a) a topical composition comprising up to about 2 weight percent of glucosamine hydrochloride, and (b) a light delivery device that delivers red light having a peak wavelength of about 600 nm to about 750 nm, near infrared light having a peak wavelength of about 750 nm to about 1000 nm, or both.

The invention further provides a topical composition comprising about 0.1 to about 2 weight percent glucosamine hydrochloride and at least one compound having a pKa of about 2.5 to about 4.5, said composition having a pH of less than about 5.5.

The invention also provides a film comprising a topical composition comprising about 0.1 to about 2 weight percent glucosamine hydrochloride and at least one compound having a pKa of about 2.5 to about 4.5, said composition having a pH of less than about 5.5.

DETAILED DESCRIPTION OF THE INVENTION

Unless defined otherwise, all technical and scientific terms used herein have the same meaning as commonly understood by one of ordinary skill in the art to which the invention belongs. All publications, patent applications, patents, and other references mentioned herein are incorporated by reference.

As used herein, "topically applying" means directly laying on or spreading on outer skin or the scalp, e.g., by use of the hands or an applicator such as a wipe, roller, or spray.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more conditions, but low enough to avoid serious side effects. The cosmetically effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

As used herein, "cosmetically acceptable" means that the ingredients the term describes are suitable for use in contact with tissues (e.g., the skin) without undue toxicity, incompatibility, instability, irritation, allergic response, or the like.

As used herein, a "cosmetically acceptable active agent" is a compound (synthetic or natural) that has a cosmetic or therapeutic effect on the skin.

As used herein, "treatment or treating" refers to mitigating, reducing, preventing, improving, or eliminating the presence or signs of a condition or disorder.

The present invention is suitable for treating signs of skin aging. As used herein, "signs of skin aging" includes the presence of lines and wrinkles, loss of elasticity, uneven skin, and blotchiness. In a particularly preferred embodiment, the sign of aging is the presence of lines and wrinkles and/or loss of elasticity.

As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

Compositions of the invention are also useful for treating skin in need of moisturization. As used herein, "skin in need of moisturization" means a skin that is, but not limited to, lacking in moisture, lacking in sebum, cracked, dry, itchy, scaly, xerodermic, dehydrated, lacks suppleness, lacks radiance, dull, or lacks lipids.

Unless otherwise indicated, a percentage or concentration refers to a percentage or concentration by weight (i.e., % (W/W). Unless stated otherwise, all ranges are inclusive of the endpoints, e.g., "from 4 to 9" includes the endpoints 4 and 9.

Topical Composition Comprising Glucosamine Hydrochloride

The invention utilizes a topical composition comprising glucosamine hydrochloride.

The topical composition may contain up to about 2 weight percent, preferably up to about 1.5 weight percent, or more preferably up to about 1 weight percent glucosamine hydrochloride.

Glucosamine is available in various forms, including various salts and derivatives. The inventors have discovered that not all glucosamine forms provide superior effects when combined with infrared and/or red light. Surprisingly, administration of glucosamine hydrochloride with infrared and/or red light synergistically increases hyaluronic acid production. This was not observed with glucosamine phosphate, N-acetyl glucosamine, or glucosamine.

Glucosamine hydrochloride is commercially available from for example Sigma Aldrich.

The composition may optionally comprise a wide variety of additional oil-soluble materials and/or water-soluble materials conventionally used in compositions for use on skin, at their art-established levels. For example, surfactants, pearlescent or opacifying agents, thickeners, emollients, conditioners, humectants, chelating agents, exfoliants, and additives that enhance the appearance, feel, or fragrance of the composition, such as colorants, fragrances, preservatives, pH adjusting agents, and the like, can be included.

The composition may comprise one or more other cosmetically acceptable active agents include for example other anti-aging agents and moisturizers, anti-acne agents, shine control agents, anti-microbial agents, anti-inflammatory agents, anti-mycotic agents, anti-parasite agents, external analgesics, sunscreens, photoprotectors, antioxidants, keratolytic agents, surfactants, nutrients, vitamins, energy enhancers, anti-perspiration agents, astringents, deodorants, firming agents, anti-callous agents, agents for skin conditioning, and agents for skin lightening.

The amount of other cosmetically active agent in may range from about 0.001% to about 20% by weight of the composition, e.g., about 0.005% to about 10% by weight of the composition, such as about 0.01% to about 5% by weight of the composition.

The cosmetically acceptable active agent may be selected for instance from, benzoyl peroxide, D-panthenol carotenoids, ceramides, polyunsaturated fatty acids, essential fatty acids, enzymes such as laccase, enzyme inhibitors, minerals, hormones such as estrogens, steroids such as hydrocortisone, 2-dimethylaminoethanol, copper salts such as copper chloride, peptides like argireline, syn-ake and those containing copper, coenzyme Q10, amino acids such as proline, vitamins, lactobionic acid, acetyl-coenzyme A, niacin, riboflavin, thiamin, ribose, electron transporters such as NADH and FADH2, natural extracts such as from aloe vera, feverfew, oatmeal, dill, blackberry, princess tree, *Picia anomala*, and chicory, resorcinols such as 4-hexyl resorcinol, curcuminoids, sugar amines such as N-acetyl glucosamine and other glucosamines beside glucosamine hydrochloride, and derivatives thereof.

Examples of vitamins include, but are not limited to, vitamin A, vitamin B's such as vitamin B3, vitamin B5, and vitamin B12, vitamin C, vitamin K, and different forms of vitamin E like alpha, beta, gamma or delta tocopherols or their mixtures, and derivatives thereof.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

In one embodiment, the topical composition comprises about at least about 4, or about 4 to about 20 weight percent glycerin, for example about 6 to about 10 weight percent glycerin.

In another embodiment, the topical composition comprises about 0.1 to about 2 weight percent glucosamine hydrochloride and at least one compound having a pKa of about 2.5 to about 4.5, said composition having a pH of less than about 5.5. For example, the compound having a pKa of about 2.5 to about 4.5 may be selected from the group consisting of citric acid, lactic acid, glycolic acid, succinic acid, and mixtures thereof.

In another embodiment the topical composition further comprises sodium bisulfite.

The composition may further include a cosmetically acceptable topical carrier. The carrier may be from about 50% to about 99.99%, by weight, of the composition (e.g., from about 80% to about 99%, by weight, of the composition). In one embodiment of the invention, the cosmetically acceptable topical carrier includes water.

The composition may be made into a wide variety of product types that include but are not limited to lotions, creams, gels, sticks, sprays, ointments, pastes, foams, powders, mousses, creams, wipes, patches, hydrogels, film-forming products, facial masks and skin masks, dissolving or non-dissolving films, and make-up such as foundations. These product types may contain a variety of cosmetically acceptable topical carriers including, but not limited to solutions, suspensions, emulsions such as microemulsions and nanoemulsions, gels, solids, films and liposomes. The following are non-limiting examples of such carriers. Other carriers can be formulated by those of ordinary skill in the art.

The composition can be formulated as a solution. Solutions typically include an aqueous or organic solvent (e.g., from about 50% to about 99.99% or from about 90% to about 99% of a cosmetically acceptable aqueous or organic solvent). Examples of suitable organic solvents include propylene glycol, polyethylene glycol, polypropylene glycol, glycerol, 1,2,4-butanetriol, sorbitol esters, 1,2,6-hexanetriol, ethanol, and mixtures thereof.

The composition may be formulated as a solution comprising an emollient. Such compositions preferably contain from about 2% to about 50% of an emollient(s). As used herein, "emollients" refer to materials used for the prevention or relief of dryness, such as by preventing the transepidermal loss of water from the skin. Examples of emollients include, but are not limited to, those set forth in the *International Cosmetic Ingredient Dictionary and Handbook*, eds. Pepe, Wenninger and McEwen, pp. 2930-36 (The Cosmetic, Toiletry, and Fragrance Assoc., Washington, D.C., 9th Edition, 2002) (hereinafter "ICI Handbook"). Examples of particularly suitable emollients include vegetable oils, mineral oils, fatty esters, and the like.

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

The composition alternatively be anhydrous or be an ointment that includes no water but organic and/or silicone solvents, oils, lipids and waxes. An ointment may contain a simple base of animal or vegetable oils or semi-solid hydrocarbons. An ointment may contain from about 2% to about 10% of an emollient(s) plus from about 0.1% to about 2% of a thickening agent(s). Examples of thickening agents include, but are not limited to, those set forth in the ICI Handbook pp. 2979-84.

The composition may be formulated as an emulsion. If the topical carrier is an emulsion, from about 1% to about 10% (e.g., from about 2% to about 5%) of the topical carrier contains an emulsifier(s). Emulsifiers may be nonionic, anionic or cationic. Examples of emulsifiers include, but are not limited to, those set forth in the ICI Handbook, pp. 2962-71.

Lotions and creams can be formulated as emulsions. Typically, such lotions contain from 0.5% to about 5% of an emulsifier(s). Such creams typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The composition can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contain between about 0.1% and 5%, by weight, of such gelling agents.

The composition can also be formulated into a solid (e.g., wax-based stick, bar, or powder).

The composition may be contained in a substrate, such as a film, woven or non-woven material, wipe, patch, mask, article of clothing and the like.

In one embodiment, the composition is contained in a film. As used herein, the term "film" means a composition that forms a thin layer or membrane on mammalian, and more particularly human skin. Such film may comprise a single layer or multiple layers.

In one embodiment, the film is a dissolvable film. A variety of dissolvable films are known in the art, and any one of these may be used according to the invention.

In one particular embodiment, the film may comprise an integral film product as described in US 2015/0182991, the disclosure of which is incorporated herein by reference.

The integral film product is arranged and configured to be removable from the manufacturing substrate it is made on, for use independent of the manufacturing substrate. In particular, the product may be made by placing a mask over a manufacturing substrate having a releasable surface, delivering a film-forming composition through the mask to form a raw shape on the manufacturing substrate; removing the mask; and solidifying the raw shape into the integral film product disposed on the manufacturing substrate. The mask has at least one aperture having a shape corresponding to the desired integral film product. The integral film product is arranged and configured to be removable from the releasable surface of the manufacturing substrate for use independent thereof.

In another embodiment, the film is a multilayered shaped film product as described in US 2015/0182990, the disclosure of which is incorporated herein by reference. For example, a two layer shaped film product comprising a first surface comprising the topical composition to be delivered to skin, and a second surface exposed to the exterior, may be used. Such an article of manufacture may be made using a process that comprises delivering liquid film-forming compositions through a mask; removing the mask to leave a multilayered raw shape; and curing the multilayered raw shape to form the multilayered shaped film product. The mask has a delivery surface, an opposite surface and at least one aperture having a design corresponding to the desired shaped film product. The film-forming compositions are delivered through a multistream nozzle. The movement of the mask and the delivery of the first and second liquid film-forming compositions to the mask aperture are controlled to provide a volumetric flow rate of the first and second liquid film-forming compositions to the mask aperture corresponding to the volume of a void. The nozzle is in contact with the delivery surface of the mask.

In another particular embodiment, the film may be multilayered film product as described in US 2015/0182992, the disclosure of which is incorporated herein by reference. For example, a two layer shaped film product in which a first layer has a larger surface area than a second layer disposed on the first layer may be used. This forms an "island" of the second layer on top of the first layer. One of the two layers is for contacting the skin and comprises the composition of the invention. The other layer is exposed to the exterior. Such an article of manufacture may be made by a process that comprises delivering a first film-forming composition through a first mask to form a first raw shape; removing the first mask; placing a second mask over the first raw shape; delivering a second film-forming composition through the second mask to form a second raw shape on the first raw shape; removing the second mask; and solidifying the first and second raw shapes to provide a shaped film product.

In a further embodiment, a shaped film product as described in US 2015/0182993, the disclosure of which is incorporated herein by reference, may contain the composition. Such shaped film product may be made by placing a mask over a manufacturing substrate; delivering a film-forming composition through a nozzle to form a raw shape on the manufacturing substrate; removing the mask; and solidifying the film-forming composition to provide the shaped film product disposed on the manufacturing substrate. The mask has a delivery surface and an opposite manufacturing substrate-facing surface and at least one aperture having a design corresponding to the desired shaped film product. The nozzle is disposed in sealing engagement with the delivery surface of the mask to the at least one aperture of the mask during delivery of the film-forming composition.

In yet another embodiment, a multilayer topically applied film as described in US 2016/0367490, the disclosure of which is incorporated herein by reference, may be used. This film is readily removable upon application of water thereto. As used herein, "readily removable" means the film may dissolve or disintegrate upon application of water to the film, such that it may be removed from the skin without scrubbing or the like.

Such a film comprises a first top layer having a first top surface for facing outwardly from the skin and a first bottom surface opposite the first top surface for facing towards the skin. The article also comprises a bottom skin-contacting layer comprising a second top surface facing and adhered to the first bottom surface of the first top layer and a second bottom surface that is outwardly-facing for contacting and adherence of the article to the skin when the article is applied thereto. The bottom skin-contacting layer comprises the topical composition. In addition, each of the first top layer and second bottom layer comprises a water-soluble film former and the article is readily removable from the skin upon application of water thereto.

This film containing the topical composition may be formed by one of the above-described processes of forming multilayer shaped film products. It may also be made by casting and drying an adhesive layer, and then casting the top layer on top of the bottom layer. The two layers may adhere to one another by any of the known methods of adhesion (mechanical, chemical, dispersive, electrostatic, diffusive, etc.). In one embodiment, the two layers preferably are both water soluble, so that the water in the non-adhesive outwardly-facing layer will slightly dissolve the already dried adhesive skin-contacting layer, thereby creating a certain amount of diffusive adhesion at the interface of the two layers. In a second embodiment, both layers are cast wet on wet, and intermixing of the materials occurs at their interface, thereby creating a bond by diffusive adhesion. Preferably, the materials have a common solvent and/or are miscible with each other so that they intermix and bond together. It will be appreciated that the materials of the adhesive and non-adhesive layers (the skin-contacting and outwardly-facing layers, respectively) may have a common solvent other than water, such as alcohol, so that the materials bond to each other.

For example, the skin-contacting layer preferably comprises a hydrophilic film-forming polymer, a solubilizing agent to solubilize other ingredients in the film, a disintegration promoter, a thickening agent/structuring agent/texture modifier, a hydroscopic agent/wetting agent to retain skin moisture, a partition coefficient modifier/absorption or permeation-promoting substances to drive the hydroscopic agent into skin, a plasticizer/primary adhesive agent for flexibility and softness, a solvent used for hydrocolloids and retain latent moisture and keep final article flexible and other auxiliaries or additives. The skin-contacting layer is applied preferably directly to the skin surface and possesses properties suitable for use as the skin-contacting surface of the article. Such properties include rapid dissolution, sustained adhesion strength, semi-occlusiveness, and flexibility. The skin-contacting layer comprises the glucosamine hydrochloride and other ingredients of the topical composition.

The outwardly-facing layer possesses proprieties suitable for use as a physical barrier, allowing it to remain clean of dust and dirt and debris while the article remains in place on the application site. Such proprieties include rapid dissolution, semi-occlusiveness, flexibility, and non-stickiness. The outwardly-facing layer comprises a hydrophilic film forming polymer, a disintegration promoter, an oil-in-water emulsifier, a wax to limit water migration from the skin-contacting layer to the topical layer, a plasticizer for flexibility and softness, a primary adhesive agent, a solvent used for hydrocolloids and to retain latent moisture and to keep the final article flexible, and other auxiliaries or additives.

In a particular embodiment of the invention, the topical composition is contained in such a multilayer, water-removable film. The film may have a thickness, for example, of up to about 2 mm. The film is placed on the skin by adhering the second bottom surface to the skin. The film is then exposed to blue light having peak wavelength of 400 nm to 460 nm using a light delivery device according to the invention. The film is maintained in place for a period of time, for example, at least 15 minutes, or at least 30 minutes, or at least 3 hours, or at least 6 hours, whereby the glucosamine hydrochloride is capable of transferring to the skin application site. The film is then removed from the application site by application of water, whereupon the film dissolves.

In a further embodiment of the above, the bottom skin-contacting layer further comprises an effective amount of an emulsifier to enhance transport of the glucosamine hydrochloride to the skin. In one embodiment, the emulsifier is a glycerine derivative. For instance, the emulsifier may be selected from the group consisting of glycerides and glycerol fatty acid esters.

Light Delivery Device

The light delivery device may comprise any source of red light or near infrared light or both. In one embodiment the light delivery device delivers both red light and near infrared light.

As used herein, "red" light means light having a peak wavelength of about 600 to about 750 nm, preferably about 600 to about 700 nm. In one embodiment, the red light has a peak wavelength of about 633 nm.

As used herein, "near infrared" light means light having a peak wavelength of about 750 to about 1000 nm, preferably about 800 to about 900 nm. In one embodiment, the near infrared light has a peak wavelength of about 830.

The light delivery device may take any form or configuration, provided it emits red light, near infrared light, or both. The light may be delivered continuously, pulsed, focused, diffuse, multi-wavelength, coherent, or non-coherent within the desired range, or at the desired wavelength(s).

In certain preferred embodiments, only red, only near infrared, or only red and near infrared light is delivered to the skin. That is, light of other wavelengths is not delivered to the skin, either by filtering of such other wavelengths or the absence of such wavelengths in the light delivered by the light delivery device.

In another such embodiment, only red light is delivered.

In a further such embodiment, only near infrared light is delivered.

In a particularly preferred embodiment, both red light and near infrared light are delivered.

The light is preferably delivered at low intensity. In one embodiment, the power delivery of light is less than about 20 mW/cm$^2$. For example, the light may be delivered at an intensity of about 1 mW/cm$^2$ to about 20 mW/cm$^2$. In another embodiment, the intensity of light is below about 1 mW/cm$^2$.

The light source may be for example one or more LEDs. The LEDs may be for example individual LED bulbs or multi-LED strips.

The device may be in the form of a shaped mask, shroud, or hood for use on the face. Alternatively, the device may be shaped for use on the body, in particular the torso, such as a shirt, vest, or the like. The device may be in the form or a patch having a circular, oval, rectangular, or other shape. Such a patch may also have an irregular shape, or a shape designed to fit a particular part of the face or body.

In one embodiment, the device comprises a lamp platform and remote battery pack as described in U.S. Pat. No. 8,771,328, the disclosure of which is incorporated by reference herein. The lamp platform for radiant lamps such as LEDs are disposed in an assembly comprising a first wall to which the lamps are affixed thereto and a second wall, closer to the skin, spaced from the first wall wherein the lamps are recessed relative thereto. The second wall comprises a reflective surface facing towards the skin and a plurality of light apertures substantially aligned with the LEDs on the first wall for communicating lamp radiation from the lamps to a user. The lamps and associated circuitry are disposed between the first and second wall so that the reflective surface is relatively smooth and seamless towards the skin. The number of lamps are minimized, as is the circuitry therefor, and other assembly materials are purposefully selected for a relatively light weight assembly resulting in enhanced user comfort during therapy sessions. The walls have a malleable rigidity for flexible adjustability relative to the user. More particularly, the walls have a concave configuration relative to the face of the user which is adjustable relative to a rest position to be expandable relative to a size of the head of the user for a close fitting and secure engagement to the user during use. The device is mounted to the user with a frame comprising an eyeglass frame or goggles including lenses for shielding the user's eyes from lamp radiation. The adjustability of the embodiments is further enhanced by the walls being pivotable relative to the support frame and where the frames may include telescopic temple arms for selective adjustability relative to the head size of the user. The device is thus supported on the patient as a wearable hands-free mask or the like. A power source communicates energy to the lamps and comprises a remote battery pack and may also include a control processor for counting the number of uses by the device for the user and for indicating a need for device replacement after a predetermined number of uses.

The platform can be secured to the head by multiple means: eyeglass frames, straps, drawstring, harness, VELCRO, turn dial or snap and buttons. As the mask is secured it can be adjusted upward, for chin to forehead coverage. It can also be adjusted outward, for side-to-side coverage. In addition, once the platform has been bent/slid to cover the face area, the distance of the platform from the skin can be adjusted for achieving a desired light intensity relative to a user's skin surface. Thus, the light therapy can be maximized in up to three physical dimensions.

The subject adjustability may be implemented through "smart" processing and sensor systems for enhanced flexibility/adjustability in the form of adjustable energy output, adjustable wavelengths, priority zones, timers, and the like. The sensors of the sensor systems will enable the subject embodiments to have the ability to evaluate the skin of the face and body of a patient with sensors for color, acne, lesion density, and the like, and plan a smart treatment, utilizing more or less energy on the priority zones. The subject embodiments can be smart from the standpoint of skin type, age, overall severity of problems and have the ability to customize the treatment accordingly.

In another embodiment, the device comprises a therapeutic lamp platform for radiant lamps such as LED's disposed in a holdable spot applicator assembly, as described in US 2016/0045758, the disclosure of which is incorporated by reference herein. The holdable spot applicator assembly includes a reflective surface facing towards a patient and a plurality of LED's for communicating lamp radiation from the lamps to a user. The lamps and the associated circuitry are housed within a holdable elongated structure.

In one embodiment, ultrasonic energy is also delivered to the skin, concurrently or in series with the light. The ultrasonic energy may be delivered by the light device or by a separate device.

In one embodiment, the light delivery device delivers both light and ultrasonic energy.

Production of Hyaluronic Acid

According to the invention, a combination of topical administration of glucosamine hydrochloride and exposure to red or near infrared light or both to skin provides an unexpected increase in the hyaluronic acid produced by such skin. It has been found that such combinations provide a synergistic boost in the amount of hyaluronic acid produced by skin relative to the amount produced by either topical administration of glucosamine hydrochloride or exposure to red and/or near infrared light alone.

In addition, combinations of red and/or near infrared light exposure with other active ingredients, including other forms of glucosamine, did not provide synergistic increases in hyaluronic acid production in skin.

In one embodiment, the combination provides at least a 1.5 fold increase in hyaluronic acid production.

Hyaluronic acid production may be measured by the following method.

Human dermal fibroblasts are maintained in flask in growth medium consisting of Dulbeccos' Modified Eagle Medium (DMEM) plus 10% fetal bovine serum, 50 units/ml penicillin and 50 µg/ml streptomycin. Cells are seeded at 10,000 cells per well in a 96 well plate in phenol-red-free Dulbeccos' Modified Eagle Medium (DMEM) plus 2% fetal bovine serum, 50 units/ml penicillin and 50 µg/ml streptomycin for 24 hours before the treatments. Glucosamine HCl or other actives were dissolved in 1×PBS at 10% stock and added into the medium at various concentrations for 48 hours. Culture media is collected at 48 hours post-treatment, and measured for HA (Hyaluronic acid) secretion using Hyaluronan ELISA kit (Echelon, cat. #K-1200) following the manufacturer protocol. To assess activity, the colorimetric chance is measured at 405 nm.

The net HA secretion of each tested treatment is calculated by the amount of the HA secretion from each respective individual treatment minus the amount of the HA secretion from the untreated treatment. Then, the fold increase provided by the combination of the treatments by light+active is calculated as the fold change in net HA secreted from the application of the combined light plus active treatment divided by the net HA secreted from the treatment by light alone.

The topical composition and the light may be administered to the skin simultaneously or sequentially. When administered sequentially, the composition and light may be administered in either order. When administered with ultrasonic energy as well, the composition, light, and ultrasonic energy may be administered simultaneously or in any order.

In one embodiment of the invention, skin in need of treatment for signs of skin aging is treated by topically applying to the skin a composition comprising about up to about 2 weight percent of glucosamine hydrochloride and exposing the skin to red light having a peak wavelength of about 600 nm to about 750 nm, near infrared light having a peak wavelength of about 750 nm to about 1000 nm, or both, using a light delivery device.

In another embodiment of the invention, skin in need of treatment for moisturization is treated by topically applying to the skin a composition comprising about up to about 2 weight percent of glucosamine hydrochloride and exposing the skin to red light having a peak wavelength of about 600 nm to about 750 nm, near infrared light having a peak wavelength of about 750 nm to about 1000 nm, or both, using a light delivery device.

The following non-limiting examples further illustrate the invention.

EXAMPLE 1

The activities of the following test treatments for production of hyaluronic acid were compared using the in vitro method described above using an untreated sample as the control: a) a combination of 633 nm red and 830 nm IR light (0.3 J/cm$^2$ each), b) a combination of 633 nm red and 830 nm IR light (3 J/cm$^2$ each), c) 0.02% glucosamine HCl in cell media solution, d) 0.2% glucosamine HCl in cell media solution, e) simultaneous application of a combination of red and IR light (0.3 J/cm$^2$ each) and 0.02% glucosamine HCl in cell media solution, and f) simultaneous application of a combination of red and IR light (3 J/cm$^2$ each) and 0.2% glucosamine HCl in cell media solution.

The results are shown in Table 1.

TABLE 1

| Treatment | HA concentrations (ng/ml) | Change in HA concentration over Untreated (ng/ml) | Fold Change versus treatment with light alone |
|---|---|---|---|
| Untreated | 551 | 0 | — |
| Red + NIR light (0.3 J/cm$^2$ each) | 1412 | +861 | — |
| Red + NIR light (3 J/cm$^2$ each) | 1828 | +1277 | — |
| 0.02% Glucosamine HCl | 543 | −8 | — |
| 0.2% Glucosamine HCl | 999 | +448 | — |
| Red + NIR Light (0.3 J/cm$^2$) + 0.02% Glucosamine HCl | 2489 | +1938 | 2.25 |

TABLE 1-continued

| Treatment | HA concentrations (ng/ml) | Change in HA concentration over Untreated (ng/ml) | Fold Change versus treatment with light alone |
|---|---|---|---|
| Red + NIR Light (3 J/cm$^2$) + 0.02% Glucosamine HCl | 4379 | +3828 | 2.99 |
| Red + NIR Light (0.3 J/cm$^2$) + 0.2% Glucosamine HCl | 2260 | +1709 | 1.98 |
| Red + NIR Light (3 J/cm$^2$) + 0.2% Glucosamine HCl | 3873 | +3322 | 2.60 |

Treatments of a combination of red and near infrared light and glucosamine HCl synergistically increased the hyaluronic acid secretion in the human dermal fibroblasts over treatment with the light alone.

EXAMPLE 2

Using the same test method as Example 1, the treatments shown in Table 2 were applied to human dermal fibroblasts. Glucosamine phosphate was used instead of glucosamine hydrochloride.

No synergy was observed.

TABLE 2

| Treatment | HA concentrations (ng/ml) | Change in HA concentration over Untreated (ng/ml) | Fold Change versus treatment with light alone |
|---|---|---|---|
| Untreated | 740 | 0 | |
| Red + NIR light (0.3 J/cm$^2$ each) | 1572 | 832 | |
| 0.02% Glucosamine phosphate | 689 | −51 | |
| Red + NIR Light (0.3 J/cm$^2$ each) + 0.02% Glucosamine Phosphate | 1037 | 297 | 0.36 |

EXAMPLE 3

Using the same test method as Example 1, the treatments shown in Table 3 were applied to human dermal fibroblasts. N-acetyl glucosamine was used instead of glucosamine hydrochloride.

No synergy was observed.

TABLE 3

| Treatment | HA concentrations (ng/ml) | Change in HA concentration over Untreated (ng/ml) | Fold Change versus treatment with light alone |
|---|---|---|---|
| Untreated | 860 | 0 | |
| Red + NIR light (0.3 J/cm$^2$ each) | 1784 | 924 | |
| 0.02% N-acetyl Glucosamine | 735 | −125 | |
| Red + NIR Light (0.3 J/cm$^2$ each) + 0.02% N-acetyl Glucosamine | 1878 | 1018 | 1.1 |

EXAMPLE 4

Topical compositions comprising glucosamine hydrochloride were prepared using the ingredients shown in Table 4 at pH values ranging from 4 to 5.5 by adjusting the amount of sodium hydroxide. Those compositions having a pH above 5.5 were not physically stable when evaluated visually for appearance and color after 7 days at 60° C. or after 30 days at 50° C.

TABLE 4

| US INCI | % wt |
|---|---|
| Water | 79.84 |
| Sodium Bisulfite | 0.1 |
| Citric Acid | 0.5 |
| Sodium Citrate | 0.13 |
| Polyacrylate Crosspolymer-6 | 0.8 |
| Chlorphenesin | 0.2 |
| Cetearyl Olivate; Sorbitan Olivate | 0.5 |
| Glycerin | 8 |
| Polyisobutene; Polysorbate 20; Polyacrylate-13 | 1.5 |
| Dimethicone; Dimethicone Crosspolymer | 1 |
| Dimethicone | 2.88 |
| Dimethicone; Dimethiconol | 1.5 |
| Ethylhexylglycerin; Phenoxyethanol | 0.8 |
| Glucosamine HCl | 1 |
| Sodium Hydroxide | 0.25 |
| Water | 1 |
| Total: | 100 |

EXAMPLE 5

Two topical compositions for use in the claimed invention were prepared using the ingredients shown in Tables 5 and 6. The topical composition of Table 5 contained 0.1% by weight sodium bisulfite. The topical composition of Table 6 did not contain sodium bisulfite.

When tested for physical stability using the method described in Example 4, the composition of Table 5 showed improved color and appearance compared with the composition of Table 6.

TABLE 5

| US INCI | % wt |
|---|---|
| Water | 79.97 |
| Sodium Bisulfite | 0.1 |
| Citric Acid | 0.5 |
| Polyacrylate Crosspolymer-6 | 0.8 |
| Chlorphenesin | 0.2 |
| Cetearyl Olivate; Sorbitan Olivate | 0.5 |
| Glycerin | 8 |
| Polyisobutene; Polysorbate 20; Polyacrylate-13 | 1.5 |
| Dimethicone; Dimethicone Crosspolymer | 1 |
| Dimethicone | 2.88 |
| Dimethicone; Dimethiconol | 1.5 |
| Ethylhexylglycerin; Phenoxyethanol | 0.8 |
| Glucosamine HCl | 1 |
| Sodium Hydroxide | 0.25 |
| Water | 1 |
| Total: | 100 |

TABLE 6

| US INCI | % wt |
|---|---|
| Water | 80.07 |
| Citric Acid | 0.5 |
| Polyacrylate Crosspolymer-6 | 0.8 |
| Chlorphenesin | 0.2 |
| Cetearyl Olivate; Sorbitan Olivate | 0.5 |
| Glycerin | 8 |
| Polyisobutene; Polysorbate 20; Polyacrylate-13 | 1.5 |
| Dimethicone; Dimethicone Crosspolymer | 1 |
| Dimethicone | 2.88 |
| Dimethicone; Dimethiconol | 1.5 |
| Ethylhexylglycerin; Phenoxyethanol | 0.8 |
| Glucosamine HCl | 1 |
| Sodium Hydroxide | 0.25 |
| Water | 1 |
| Total: | 100 |

The compositions of Table 7 were also prepared. Compositions A and B contained either BHT or Tocopheryl Acetate, known antioxidants, instead of sodium bisulfite (Composition C). However, neither Composition A nor Composition B showed improvement in physical stability versus Composition C when tested in the manner set forth in Example 4.

TABLE 7

| US INCI | A % wt | B % wt | C % wt |
|---|---|---|---|
| Water | 80.62 | 80.69 | 80.64 |
| Disodium EDTA | 0.2 | 0.2 | 0.2 |
| BHT | 0.12 | — | — |
| Tocopheryl Acetate | — | 0.05 | — |
| Sodium Bisulfite | — | — | 0.1 |
| Polyacrylate Crosspolymer-6 | 0.8 | 0.8 | 0.8 |
| Chlorphenesin | 0.2 | 0.2 | 0.2 |
| Cetearyl Olivate; Sorbitan Olivate | 0.5 | 0.5 | 0.5 |
| Glycerin | 8 | 8 | 8 |
| Polyisobutene; Polysorbate 20; Polyacrylate-13 | 1.5 | 1.5 | 1.5 |
| Dimethicone; Dimethicone Crosspolymer | 1 | 1 | 1 |
| Dimethicone | 3.5 | 3.5 | 3.5 |
| Dimethicone; Dimethiconol | 1.5 | 1.5 | 1.5 |
| Ethylhexylglycerin; Phenoxyethanol | 0.8 | 0.8 | 0.8 |
| Glucosamine HCl | 1 | 1 | 1 |
| Sodium Hydroxide | 0.13 | 0.13 | 0.13 |
| Water | 0.13 | 0.13 | 0.13 |
| Total: | 100 | 100 | 100 |

The invention claimed is:

1. A method of treating skin, comprising topically applying to skin in need of treatment for signs of skin aging a topical composition comprising up to about 2 weight percent of glucosamine hydrochloride, and exposing said skin to both red light having a peak wavelength of about 600 nm to about 750 nm and near infrared light having a peak wavelength of about 750 nm to about 1000 nm, using a light delivery device, wherein the intensity of the light is below about 20 mW/cm$^2$.

2. The method of claim 1, wherein the signs of skin aging are fine lines and wrinkles.

3. The method of claim 1, wherein the topical composition has a pH of about 3.0 to about 5.5.

4. The method of claim 1 further comprising exposing said skin to ultrasonic energy.

5. The method of claim 4, wherein the light delivery device delivers light and ultrasonic energy.

6. A method of treating skin, comprising topically applying to skin in need of moisturization a topical composition comprising up to about 2 weight percent of glucosamine hydrochloride, and exposing said skin to both red light having peak wavelength of about 600 nm to about 750 nm and near infrared light having a peak wavelength of about 750 nm to about 1000 nm, using a light delivery device, wherein the intensity of the light is below about 20 mW/cm$^2$.

7. The method of claim 6, wherein the signs of skin aging are fine lines and wrinkles.

8. The method of claim 6, wherein the topical composition has a pH of about 3.0 to about 5.5.

9. The method of claim 6 further comprising exposing said skin to ultrasonic energy.

10. The method of claim 9, wherein the light delivery device delivers light and ultrasonic energy.

* * * * *